US012800509B2

(12) United States Patent
Niizuma et al.

(10) Patent No.: US 12,800,509 B2
(45) Date of Patent: Nov. 17, 2026

(54) SURFACE INSPECTION METHOD FOR METAL MATERIAL, SURFACE INSPECTION APPARATUS FOR METAL MATERIAL, AND METAL MATERIAL

(71) Applicant: JFE STEEL CORPORATION, Tokyo (JP)

(72) Inventors: Yuya Niizuma, Tokyo (JP); Hiroaki Ono, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 54 days.

(21) Appl. No.: 18/729,440

(22) PCT Filed: Jan. 31, 2023

(86) PCT No.: PCT/JP2023/003026
§ 371 (c)(1),
(2) Date: Jul. 16, 2024

(87) PCT Pub. No.: WO2023/166898
PCT Pub. Date: Sep. 7, 2023

(65) Prior Publication Data
US 2025/0116609 A1 Apr. 10, 2025

(30) Foreign Application Priority Data
Mar. 3, 2022 (JP) ................................ 2022-032278

(51) Int. Cl.
*G01N 33/2045* (2019.01)
*G01N 21/31* (2006.01)
*G01N 21/88* (2006.01)

(52) U.S. Cl.
CPC ......... *G01N 21/8806* (2013.01); *G01N 21/31* (2013.01); *G01N 33/2045* (2019.01)

(58) Field of Classification Search
CPC ............... G01N 33/2045; G01N 21/89; G01N 21/8914; G01N 21/892; G01N 21/8851;
(Continued)

(56) References Cited

U.S. PATENT DOCUMENTS 6,327,374 B1 * 12/2001 Piironen ................ G01N 21/57 382/108
10,180,401 B2 * 1/2019 Ono ........................ G06F 18/24
(Continued)

FOREIGN PATENT DOCUMENTS

JP S59-52735 A 3/1984
JP H04-031753 A 2/1992
(Continued)

OTHER PUBLICATIONS

May 7, 2025 Office Action issued in Japanese Patent Application No. 2023-528049.
(Continued)

*Primary Examiner* — Abdullahi Nur
(74) *Attorney, Agent, or Firm* — Oliff PLC

(57) ABSTRACT

A surface inspection method for a metal material in which a surface defect of the metal material is optically detected, the surface inspection method includes: (a) irradiating a surface of the metal material with light; (b) obtaining a plurality of images by capturing reflected light from the surface of the metal material by the light emitted in (a) in two or more different wavelengths bands; and (c) detecting the surface defect present on the surface of the metal material from information of a relative signal intensity between the plurality of images obtained from a same position on the surface of the metal material in (b).

18 Claims, 5 Drawing Sheets

(58) Field of Classification Search
CPC .... G01N 21/8806; G01N 21/31; G01N 21/25; G01N 2021/8845; G01N 2021/8918; G01N 2021/8858; G06N 20/00
See application file for complete search history.

(56) References Cited

U.S. PATENT DOCUMENTS

| | | | | |
|---|---|---|---|---|
| 10,705,027 | B2 | 7/2020 | Ono et al. | |
| 11,022,553 | B2 * | 6/2021 | Richard | G01N 21/8901 |
| 11,199,504 | B2 * | 12/2021 | Konno | G01N 21/8901 |
| 2010/0091272 | A1 * | 4/2010 | Asada | G01N 21/55 356/237.2 |
| 2017/0122878 | A1 | 5/2017 | Ono et al. | |
| 2018/0350060 | A1 * | 12/2018 | Nakao | G06T 7/194 |
| 2019/0011375 | A1 | 1/2019 | Ono et al. | |
| 2019/0318469 | A1 * | 10/2019 | Wang | G01N 21/4788 |
| 2020/0134773 | A1 * | 4/2020 | Pinter | G01N 21/8806 |
| 2021/0193350 | A1 | 6/2021 | Tsuchida et al. | |
| 2023/0349836 | A1 * | 11/2023 | Yoshida | G01N 21/892 |

FOREIGN PATENT DOCUMENTS

| | | | | |
|---|---|---|---|---|
| JP | H04-113260 | A | 4/1992 | |
| JP | H11-37949 | A | 2/1999 | |
| JP | H11-337502 | A | 12/1999 | |
| JP | 2005207858 | A * | 8/2005 | |
| JP | 2010-266430 | A | 11/2010 | |
| JP | 2011-191252 | A | 9/2011 | |
| JP | 2014020926 | A * | 2/2014 | |
| JP | 5659540 | B2 | 1/2015 | |
| JP | 2015-125089 | A | 7/2015 | |
| JP | 6079948 | B1 | 2/2017 | |
| JP | WO2016208626 | A1 * | 6/2017 | G01N 21/8901 |
| JP | 2018-036175 | A | 3/2018 | |
| JP | 6769182 | B2 | 10/2020 | |
| TW | M594136 | U | 4/2020 | |
| WO | WO-2009099142 | A1 * | 8/2009 | G01N 21/956 |
| WO | 2013/012106 | A1 | 1/2013 | |
| WO | 2021/149588 | A1 | 7/2021 | |

OTHER PUBLICATIONS

Nov. 2, 2023 Office Action issued in Taiwanese Patent Application No. 112104422.

Apr. 23, 2024 Office Action issued in Japanese Patent Application No. 2023-528049.

Apr. 4, 2023 International Search Report issued in International Patent Application No. PCT/JP2023/003026.

Feb. 6, 2025 Extended European Search Report issued in European Patent Application No. 23763160.1.

Jul. 16, 2026 Office Action issued in Korean Patent Application No. 10-2024-7025500 (with concise statement of relevance in English).

* cited by examiner

SURFACE INSPECTION METHOD FOR METAL MATERIAL, SURFACE INSPECTION APPARATUS FOR METAL MATERIAL, AND METAL MATERIAL

FIELD

The present invention relates to a surface inspection method for a metal material that optically detects a surface defect of the metal material, a surface inspection apparatus for a metal material, and a metal material.

BACKGROUND

In recent years, in manufacturing processes of metal materials, particularly steel products, it is required to detect surface defects of hot or cold steel materials from the viewpoint of improving the yield by preventing a large amount of nonconformity. The steel materials described herein means steel products including seamless steel pipes, welded steel pipes, hot-rolled steel sheets, cold-rolled steel sheets, steel plates, and shape steel bars, and semi-products such as slabs produced in a process of manufacturing these steel products. Therefore, as a method for detecting a surface defect of a steel material, a method has been proposed in which a billet in a process of manufacturing a seamless steel pipe is irradiated with light to receive the reflected light, and the presence or absence of a surface defect is determined by an amount of the reflected light (see Patent Literature 1). In addition, a method has also been proposed in which a hot steel material is irradiated with visible lights in a plurality of wavelength ranges that do not affect each other and that do not affect the light of the glow radiated from a hot steel material from oblique directions symmetric with respect to a normal line of a surface of the hot steel material, combined and individual images of reflected lights are obtained in the normal direction of the surface of the hot steel material, and a surface defect of the hot steel material is detected from a combination of these images (see Patent Literature 2). In addition, there has also been proposed a method of detecting a surface defect of a steel material in which a surface of the steel material is irradiated with mutually distinguishable illumination lights from symmetrically inclined directions with respect to a normal line of a surface of the steel material, two images are obtained by capturing an inspection target site illuminated from each of the directions to get a difference image of two images, and, from the difference image, an array of a bright portion and a dark portion corresponding to a concave shape is extracted (see Patent Literature 3).

CITATION LIST

Patent Literatures

Patent Literature 1: Japanese Unexamined Patent Application Publication No. H11-37949

Patent Literature 2: Japanese Unexamined Patent Application Publication No. S59-52735

Patent Literature 3: Japanese Patent No. 6079948

SUMMARY

Technical Problem

According to the method described in Patent Literature 1, since a reflectance of a scale or a harmless pattern is different from a reflectance of a base steel portion, there is a possibility that the scale or the harmless pattern generated in a sound portion that is not a surface defect is erroneously detected as a surface defect. For this reason, in the method described in Patent Literature 1, the surface defect and the scale are discriminated by utilizing a fact that a shape of the surface defect (surface flaw) of the billet is linear. However, the surface defects of the steel material are not limited to linear defects, and includes defects having various shapes such as circular shapes. Therefore, it is difficult to apply the method described in Patent Literature 1 to detection processing for the surface defect of the steel material. On the other hand, in the method described in Patent Literature 2, since there are many types of surface defects, scales, harmless patterns, and the like, it is difficult to discriminate the scale, the harmless patterns, and the surface defects only by simply combining the images. In addition, it is practically difficult to construct a detection logic corresponding to a huge amount of combinations of the images. In addition, according to the method described in Patent Literature 3, it is possible to solve the above problem and to accurately detect the recessed defect on the surface of the steel material. However, the surface defect of the steel material is not limited to the recessed surface defect, and there is also a defect in which no apparent unevenness of the surface is observed when rolling is performed in a state where foreign matters are embedded or when a scale is generated in a recessed defect portion. Therefore, it is difficult to completely detect surface defects generated in the steel material only by the method described in Patent Literature 3.

The present invention has been made in view of the above problems, and an object of the present invention is to provide a surface inspection method and a surface inspection apparatus for a metal material capable of detecting a surface defect of the metal material completely and accurately. In addition, another object of the present invention is to provide a high-quality metal material free from surface defects.

Solution to Problem

To solve the problem and achieve the object, a surface inspection method for a metal material according to the present invention is a method in which a surface defect of the metal material is optically detected. The surface inspection method includes: an irradiating step of irradiating a surface of the metal material with light; an image capturing step of obtaining a plurality of images by capturing reflected light from the surface of the metal material by the light emitted in the irradiating step in two or more different wavelength bands; and a detecting step of detecting the surface defect present on the surface of the metal material from information of a relative signal intensity between the plurality of images obtained from a same position on the surface of the metal material in the image capturing step.

Moreover, the detecting step may include a step of detecting the surface defect using a determiner created by a machine learning method using: a relative intensity between the plurality of images as a feature amount; or a plurality of amounts calculated from the relative intensity as the feature amount.

Moreover, the irradiating step may include a step of irradiating the metal material with the light so that an angle with respect to a normal direction of the surface of the metal material falls within a range of 60° or more and less than 90°, and the image capturing step may include a step of receiving the reflected light so that a light receiving angle with respect to the surface of the metal material falls within a range of 0° or more and less than 20°.

Moreover, at least one of the two or more different wavelength bands may be a wavelength band of 500 nm or less.

Moreover, at least one of the two or more different wavelength bands may be a wavelength band of 650 nm or more.

Moreover, a surface inspection apparatus for a metal material according to the present invention is an apparatus that optically detects a surface defect of the metal material. The surface inspection apparatus includes: irradiation means for irradiating a surface of the metal material with light; image capturing means for obtaining a plurality of images by capturing reflected light from the surface of the metal material by the light emitted by the irradiation means in two or more different wavelength bands; and detecting means for detecting the surface defect present on the surface of the metal material from information of a relative signal intensity between the plurality of images obtained from a same position on the surface of the metal material by the image capturing means.

Moreover, a metal material according to the present invention is a metal material whose surface property is guaranteed using the surface inspection method for a metal material according to the present invention.

Advantageous Effects of Invention

According to the surface inspection method and the surface inspection apparatus for a metal material according to the present invention, it is possible to detect a surface defect of the metal material completely and accurately. In addition, according to a metal material according to the present invention, it is possible to provide a high-quality metal material free from surface defects.

DESCRIPTION OF EMBODIMENTS

Figure 1:
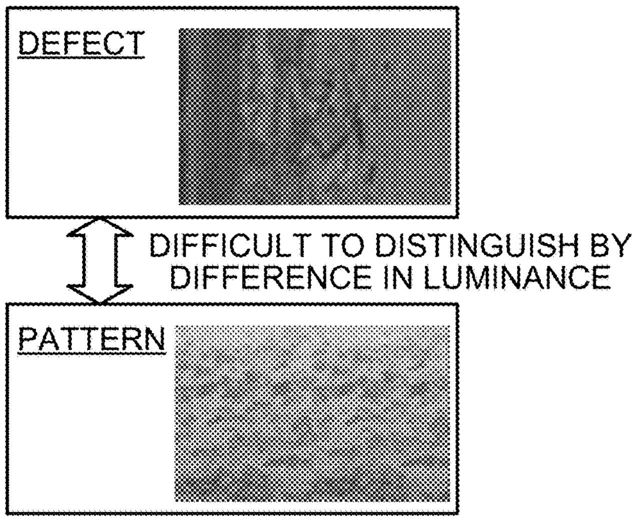
FIG. 1 is a view illustrating one example of a pattern-like defect and a harmless pattern.
Figure 2:
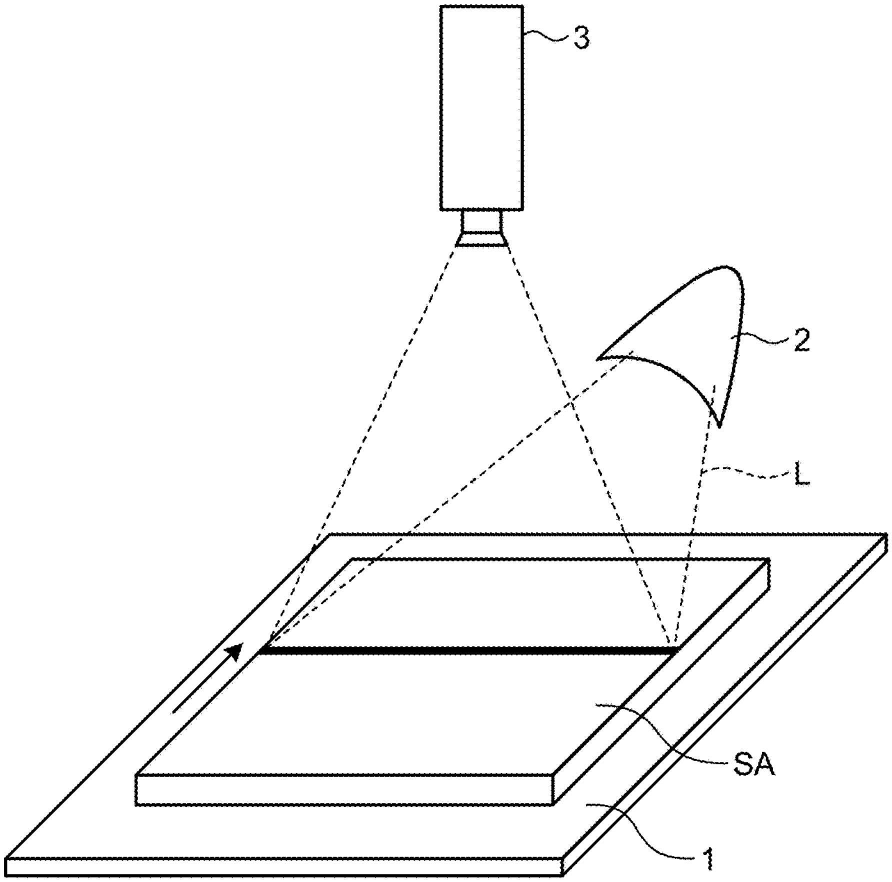
FIG. 2 is a schematic view illustrating a configuration of an apparatus used for a test.

A steel plate is a type of steel product, and its surface is covered with an oxide film called a mill scale, which may generate a pattern called a harmless pattern that does not affect quality of the steel product. In addition, a pattern-like defect such as a scab also occurs on the surface of the steel plate, but it is difficult to distinguish between the pattern-like defect and the harmless pattern by a difference in luminance as illustrated in FIG. 1. Therefore, the inventors of the present invention have focused on a fact that a minute red scale ($Fe_2O_3$) is easily generated on the pattern-like defect, and the pattern-like defect looks reddish due to this red scale, and the inventors conducted a test for detecting the pattern-like defect using spectral reflection characteristics. A configuration of an apparatus used for the test is illustrated in FIG. 2. As illustrated in FIG. 2, in this test, a thick steel plate sample SA having a pattern-like defect was placed on a linear stage 1, a surface of the thick steel plate sample SA was irradiated with illumination light L having a broadband wavelength from a xenon light source 2, and a spectral image of each wavelength was captured using a spectroscopic camera 3 having a one-dimensional field of view.

Figure 3:
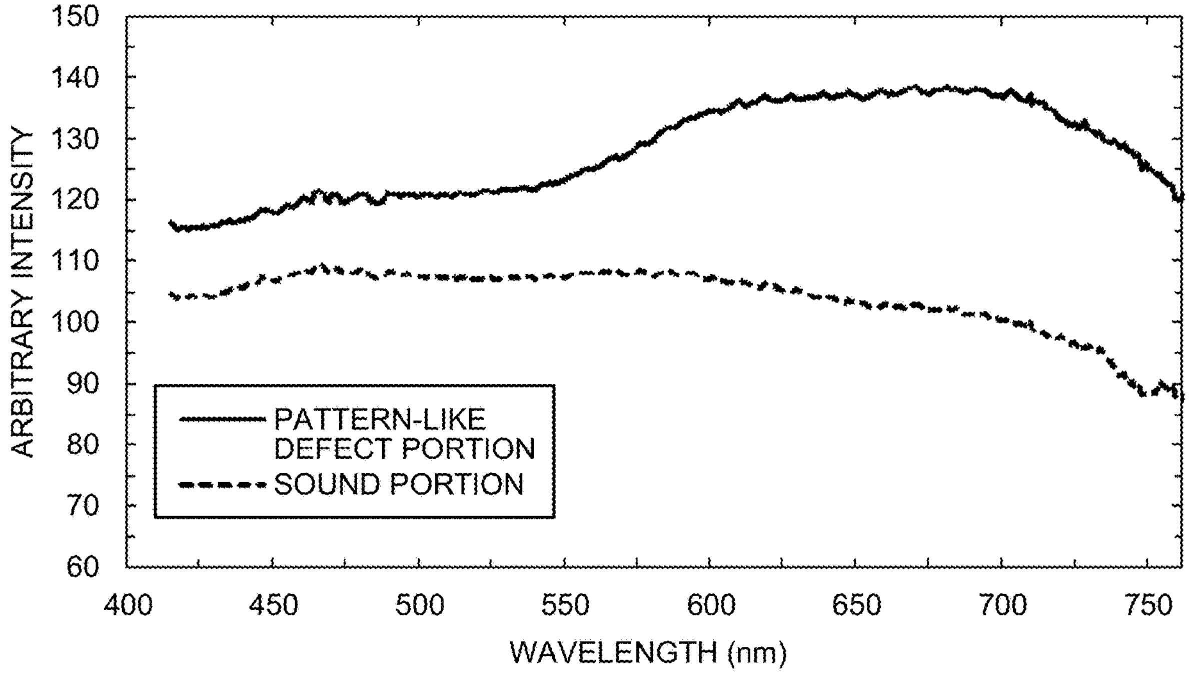
FIG. 3 is a diagram illustrating a result of comparing a relationship between a signal intensity and a wavelength for a pattern-like defect portion and a sound portion.
Figure 8:
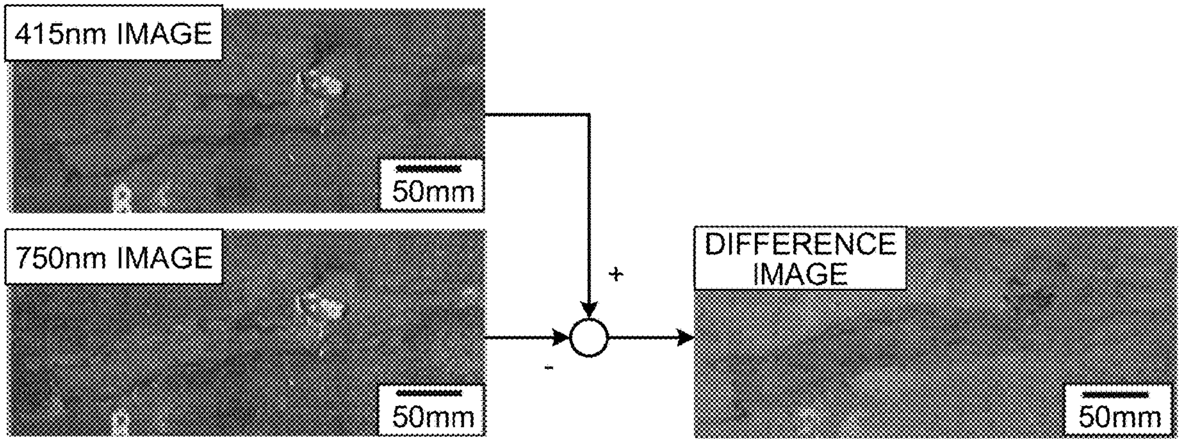
FIG. 8 is a view illustrating one example of a difference image.

FIG. 3 illustrates a result of comparing a relationship between a signal intensity and a wavelength for a pattern-like defect portion and a sound portion using the spectral image. As illustrated in FIG. 3, a characteristic of the signal intensity at a shorter wavelength and a characteristic of the signal intensity at a longer wavelength for the pattern-like defect portion is relatively different from that for the sound portion. A pattern-like defect has been difficult to detect only with a signal at a single wavelength because of interference from a signal of a harmless pattern. The above-mentioned results suggest that the pattern-like defect can be detected by comparing signal intensities at different wavelengths. For a spectral image at a wavelength band of 415 nm (415 nm image) and a spectral image at a wavelength band of 750 nm (750 nm image), a luminance correction is carried out so that average values of luminance become the same to each other, and then taking a difference between luminance values of the two spectral images, to obtain an image as illustrated in FIG. 8. FIG. 8 shows that the signal of the harmless pattern is canceled out by taking the difference, and that a signal of the pattern-like defect is emphasized.

Figure 4:
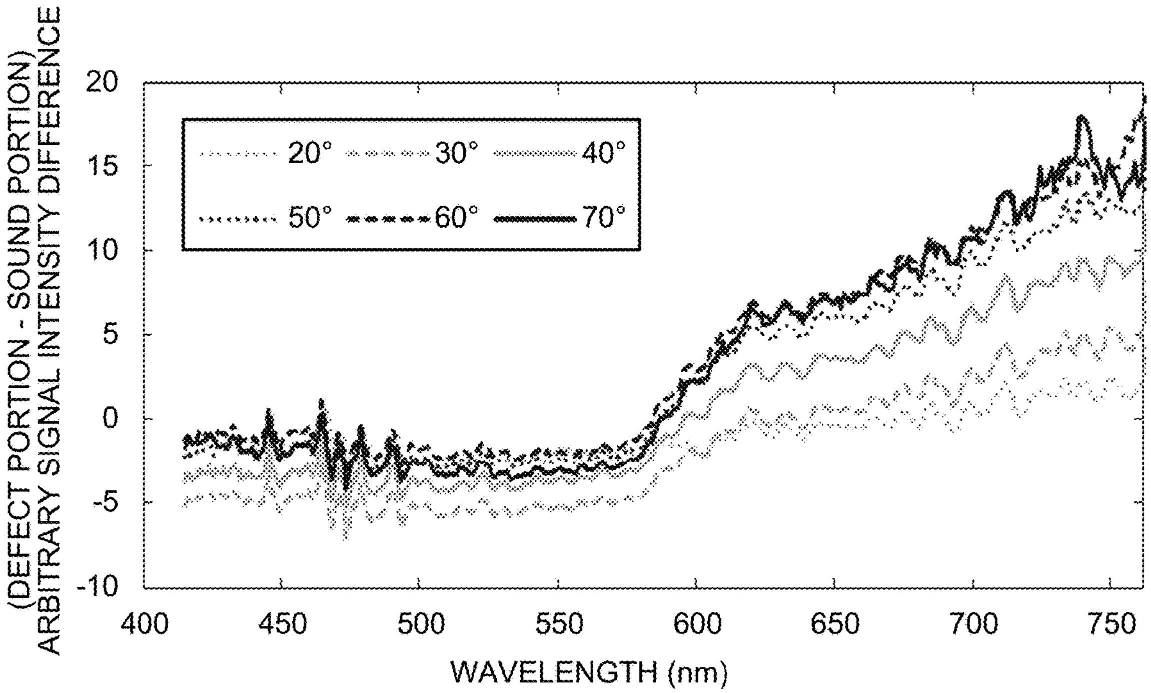
FIG. 4 is a diagram illustrating a result of comparing a relationship among an incident angle of illumination light, a signal intensity difference between a pattern-like defect portion and a sound portion, and a wavelength.

From the above, it was confirmed that the pattern-like defect having the spectral reflection characteristics different from those of the sound portion can be accurately detected by comparing luminance information between the plurality of wavelengths. In addition, FIG. 4 illustrates a result of comparison among an incident angle of the illumination light L (an angle with respect to a surface normal vector of the steel plate), a signal intensity difference between the pattern-like defect portion and the sound portion, and the wavelength. In a legend of FIG. 4, the incident angles are described as 20°, 30°, and the like. As illustrated in FIG. 4, a signal intensity difference between the shorter wavelength and the longer wavelength increases as the incident angle of the illumination light L increases. Therefore, in order to efficiently detect the spectral reflection characteristic of the target, that is, a difference in hue, it is preferable to increase the incident angle of the illumination light L. In the above description, the pattern-like defect of the steel plate has been described, but the present invention can be applied to detection of a surface defect having different spectral reflection characteristics from those of a sound portion, which is generated on a surface of another metal material.

Hereinafter, a surface inspection apparatus for a metal material, which is one embodiment of the present invention conceived from the above-described technical idea, will be described with reference to FIGS. 5 to 8.

Figure 5:
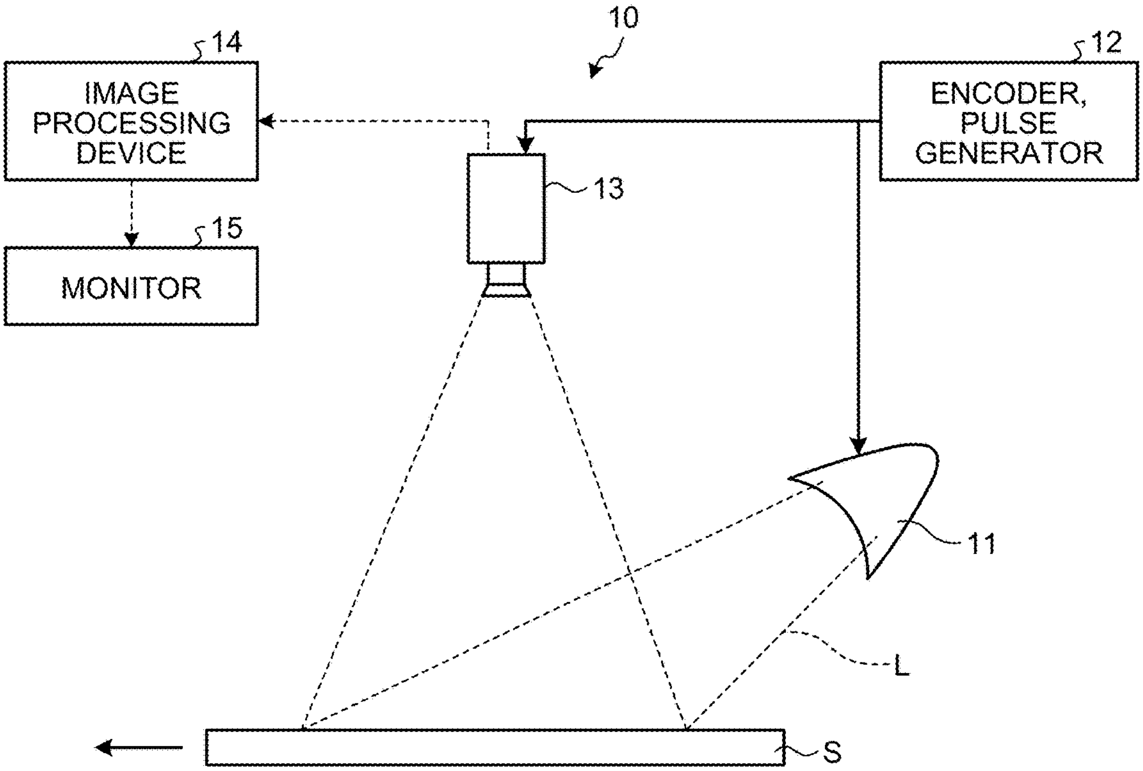
FIG. 5 is a schematic view illustrating a configuration of a surface inspection apparatus for a metal material according to a first embodiment of the present invention.

FIG. 5 is a schematic diagram illustrating a configuration of the surface inspection apparatus for a metal material according to a first embodiment of the present invention. As illustrated in FIG. 5, a surface inspection apparatus for a metal material 10 according to the first embodiment of the present invention is an apparatus that detects a surface defect of a plate-shaped steel material S conveyed in an arrow direction in the drawing. The surface inspection apparatus for a metal material 10 according to the first embodiment of the present invention includes a light source 11, an encoder and pulse generator 12, an area sensor 13 capable of capturing spectral images at a plurality of wavelength bands, an image processing device 14, and a monitor 15 as main components.

The light source 11 irradiates an inspection target site on a surface of the steel material S with the illumination light L in accordance with a trigger signal output from the pulse generator each time a pulse signal is transmitted a certain number of times from the encoder. The light source 11 may be disposed so that an irradiation direction of the illumination light L is inclined within a range of 60° or more and less than 90° with respect to a normal direction of the surface of the steel material S. Consequently, the surface defect can accurately be detected from a difference image. In addition, although the one light source 11 is disposed in the present embodiment, a plurality of light sources 11 may be disposed. In the present embodiment, a xenon light source is employed as the light source 11. However, as long as components at a plurality of different wavelength bands are included, a light source having broadband characteristics such as a metal halide lamp, a halogen lamp, a mercury lamp, or an incandescent lamp may be used, or a light source having specific narrow band characteristics such as an LED or a laser may be combined. In addition, in a case where a conveyance speed of the steel material S is high, or where a positional fluctuation of the steel material S from a determined conveyance position (a pass line) is large, or the like, a flash lamp or pulse lighting may be used to prevent image capturing blur.

The area sensor 13 captures spectral images at a plurality of wavelength bands at a substantially same position of the steel material S. The plurality of captured spectral images are preferably coaxial, but may be aligned by image processing. In addition, examples of the area sensor 13 include a Bayer type and a prism type: in a Bayer type, a filter that transmits different wavelength bands is attached so as to be nested in each element and a plurality of images is generated later; in a prism type, adjustment is performed so that the spectral images are coaxial using a prism and a plurality of elements. In addition, although it is inexpensive and preferable to use an RGB color camera, a multiband area sensor having two channels, or four or more channels may be used. Furthermore, depending on the spectral reflection characteristics of the sound portion and the surface defect portion to be discriminated, a wavelength selection filter may be installed on an optical path of a front surface of the area sensor 13 or the light source 11, or the like to enhance a color tone and improve detectability. In addition, in a case where a difference in the spectral reflection characteristics between the sound portion and the surface defect portion appears in a narrow band, a wavelength band to be received by the wavelength selection filter or the like may be set as the narrow band if there is a margin in light amount. When the pattern-like defect is to be detected, it is preferable that at least one of the plurality of wavelength bands includes a narrow wavelength band of 650 nm or more, and at least one of the plurality of wavelength bands includes a narrow wavelength band of 500 nm or less.

The area sensor 13 captures the spectral images in synchronization with the light source 11 in accordance with the trigger signal output from the pulse generator. It is assumed that the luminance value of each channel of the spectral images is not saturated except for the spectral image in which an end portion of the steel material S is captured. Further, in the present embodiment, the two-channel area sensor that captures light in the longer wavelength band and the shorter wavelength band is used, but an apparatus configuration in which three or more wavelength bands are separately captured by a three or more-channel area sensor may be adopted. Further, the area sensor 13 preferably receives the reflected light so that a light receiving angle with respect to the normal direction of the surface of the steel material S falls within a range of 0° or more and less than 20°.

The image processing device 14 detects the surface defect in the inspection target site by performing difference processing to be described later between the spectral images input from the respective channels of the area sensor 13. Then, the image processing device 14 outputs, to the monitor 15, the spectral image input from the area sensor 13, the spectral image after the difference processing, and information regarding a detection result of the surface defect.

Second Embodiment

Figure 6:
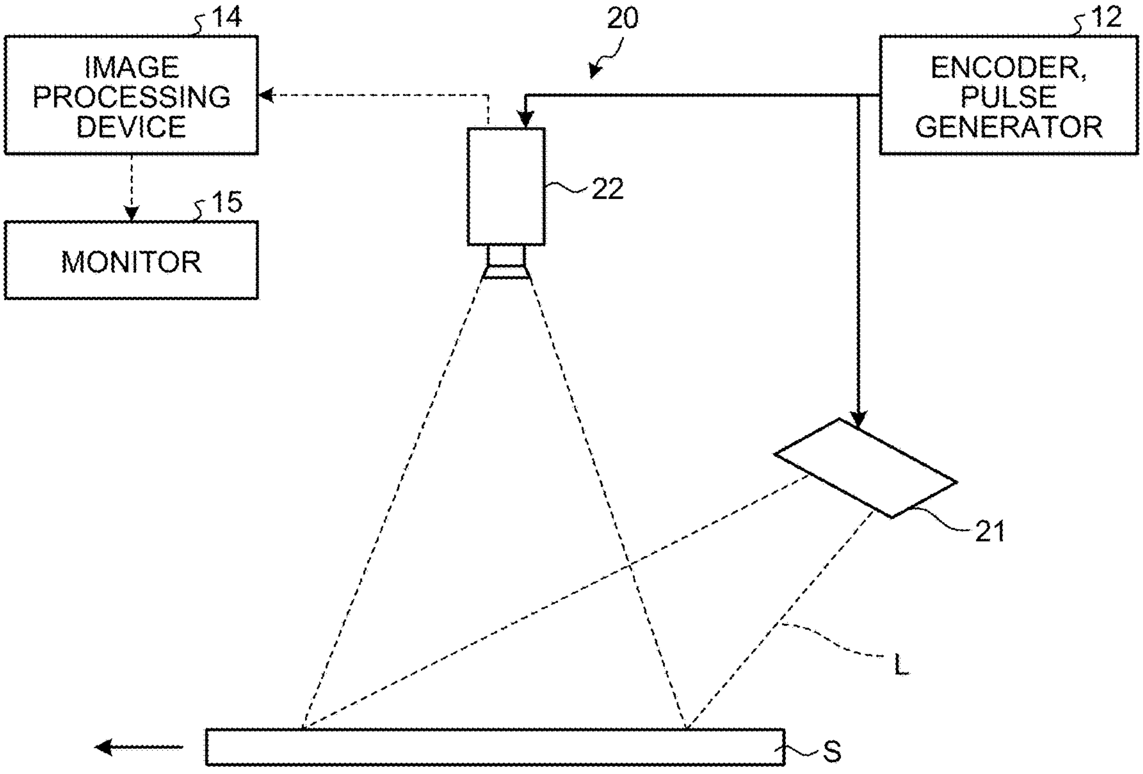
FIG. 6 is a schematic view illustrating a configuration of a surface inspection apparatus for a metal material according to a second embodiment of the present invention.

FIG. 6 is a schematic view illustrating a configuration of a surface inspection apparatus for a metal material according to a second embodiment of the present invention. As illustrated in FIG. 6, a surface inspection apparatus 20 for a metal material according to the second embodiment of the present invention detects a surface defect of a plate-shaped steel material S conveyed in an arrow direction in the drawing. A difference from the surface inspection apparatus for a metal material 10 according to the first embodiment is that the light source 11 is replaced with a line light source 21, and the area sensor 13 is replaced with a line sensor 22. When the line sensor 22 is used, its visual field is only along a straight line, and there is an advantage that an optical condition is stabilized as compared with the first embodiment. However, there is also a disadvantage that the line sensor is weak against positional fluctuation of the steel material S from the conveyance position (path line) during conveyance, or the like.

The surface inspection apparatuses for a metal material 10, 20 having such configurations execute surface inspection processing described below to discriminate between the pattern-like defect portion and the sound portion having the harmless pattern in the inspection target site. The pattern-like defect described herein is a defect in which there is no apparent unevenness from the surface due to embedding of a foreign substance, generation of a scale on a concave defect, or the like. In addition, the sound portion having the harmless pattern means a portion having surface coating or a surface property different in optical characteristics from a base steel portion having a thickness of about several to several tens μm such as a mill scale; the sound portion having the harmless patter is then a portion that becomes a noise factor in the surface inspection processing.

[Surface Inspection Processing]

Figure 7:
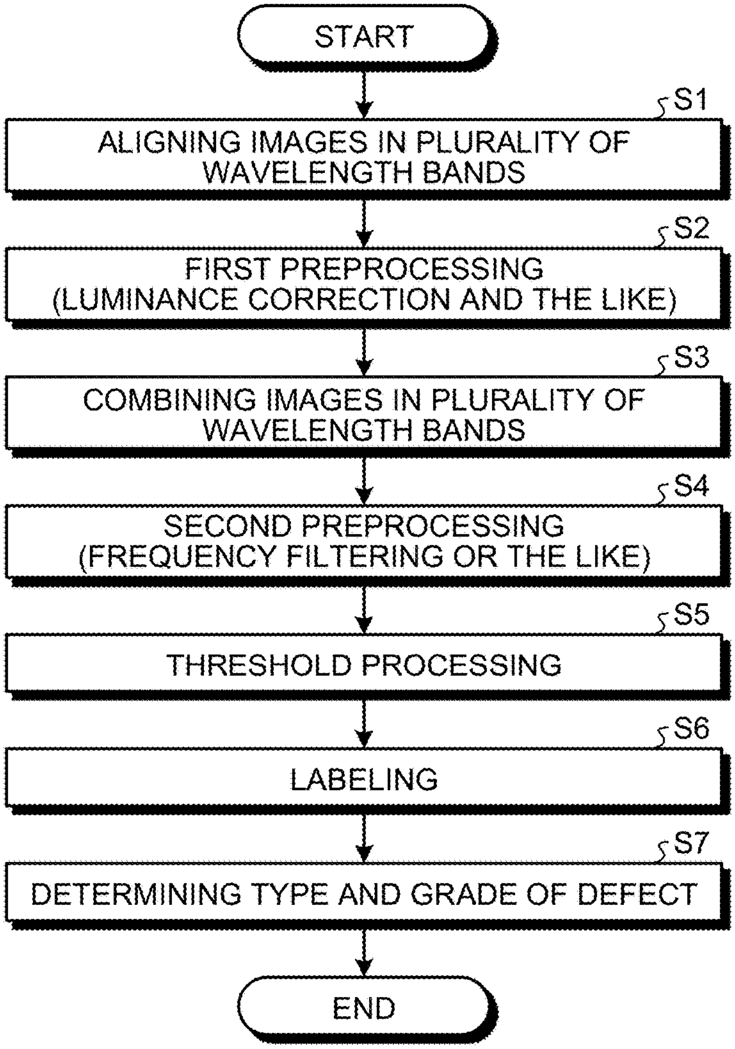
FIG. 7 is a flowchart illustrating a flow of surface inspection processing according to one embodiment of the present invention.

FIG. 7 is a flowchart illustrating a flow of the surface inspection processing according to one embodiment of the present invention. The surface inspection processing illustrated in FIG. 7 starts at timing when an execution command of the surface inspection processing is input to the image processing device 14, and the surface inspection processing proceeds to processing of Step S1.

In the processing of Step S1, in a case where positions of the spectral images of the plurality of wavelength bands are shifted in units of pixels, the image processing device 14 performs alignment processing. In a case where the spectral images cannot be coaxially captured, alignment is required among the spectral images at the plurality of wavelength bands. An alignment method changes depending on a form of the positional shift of the spectral image at each of the wavelength bands, and processing such as translation, linear conversion, and one-to-one correspondence of pixels may be executed as necessary. As a result, the processing of Step S1 is completed, and the surface inspection processing proceeds to processing of Step S2.

In the processing of Step S2, the image processing device 14 executes first preprocessing such as correction for making the average values of the luminance on the plurality of spectral images at different wavelength bands to a same value, luminance unevenness correction, and signal intensity normalization processing. As a result, the processing of Step S2 is completed, and the surface inspection processing proceeds to processing of Step S3.

In the processing in Step S3, the image processing device 14 compares the plurality of spectral images at different wavelength bands, and it generates a composite processed image in which only the pattern-like defect is emphasized by utilizing the difference in the spectral reflection characteristics. Specifically, the image processing device 14 selects two spectral images having a large difference in the spectral reflection characteristics, and calculates a difference, a ratio, or the like in luminance between the two spectral images to generate the composite processed image. A case where a difference image between the two spectral images is generated as the composite processed image will be described. In this case, the image processing device 14 subtracts a luminance value of a second spectral image Ir (for example, a luminance value Ir(x, y) of a second channel having a sensitivity characteristic corresponding to the wavelength band on the longer wavelength) from a luminance value of a first spectral image Ib (for example, a luminance value Ib(x, y) of a first channel having a sensitivity characteristic corresponding to the wavelength band on the shorter wavelength side) to calculate a luminance value Id1(*x, y*) of a difference image Id1 as expressed in formula (1) below.

$$Id1(x, y) = Ib(x, y) - Ir(x, y) \quad (1)$$

The spectral images Ib, Ir are images of a number of pixels X×Y. In addition, in an orthogonal biaxial xy coordinate system set for each of the spectral images Ib and Ir, an x coordinate is 1≤x≤X, and a y coordinate is 1≤y≤Y. Furthermore, in the present example, the difference image is generated as the composite processed image, but an image having a ratio of the luminance values using formula (2) described below may be generated as the composite processed image. Besides, after threshold processing may be separately executed on the luminance values of the two spectral images, AND processing may be performed to generate a composite processed image.

$$Id1(x, y) = Ib(x, y)/Ir(x, y) \quad (2)$$

The present processing can be executed only with the two spectral images, and techniques (a) to (c) described below are particularly effective for three or more spectral images. As a result, the processing of Step S3 is completed, and the surface inspection processing proceeds to processing of Step S4.

(a) Spatial Conversion Method

This method is effective for three channels, particularly color images, and is a method for generating an image from which an influence of the spectral reflection characteristics (color tone) is extracted by conversion of a color space. The color space after the conversion includes an HSV space or an HLS space, and information of the spectral reflection characteristics appears in hue information. In addition, after conversion into XYZ color space, L* u* v* color space, and L* a* b* color space, followed by normalization of luminance components, threshold processing may be performed on a luminance value of an image of each color.

(b) Statistical Multivariate Analysis Method

This is a method in which a luminance value at each of the wavelength bands of each pixel is used as a feature vector, and a portion having different spectral reflection characteristics is extracted by statistical multivariate analysis. As one example, a target inspection region is divided sufficiently largely, a principal component analysis (PCA) is performed using a luminance value at each of the wavelength bands of all pixels in each region as the feature vector, and an image is reconstructed using a Mahalanobis distance of each pixel as a representative value of the pixel. Since the pattern-like defect portion has a different color tone, the Mahalanobis distance is expected to be larger than that of the sound portion. The principal component analysis has been described here, but even when a deviation degree from a model is similarly calculated using a Gaussian mixture model, independent component analysis, or a regression model, a similar effect can be obtained.

(c) Machine Learning Method

This method is the same as the statistical multivariate analysis method up to the point that the luminance value at each of the wavelength bands of each pixel is used as the feature vector, but the method is a method in which the pattern-like defect portion or the sound portion is supervised for each of the feature vectors in advance, a determination apparatus is created by general supervised learning, and it is determined for each pixel whether it is the pattern-like defect portion or the sound portion. As a method of clustering the feature amount, k-means method, a kernel method, a decision tree method, a Gaussian mixture model, a regression model, or the like may be used. In a case where the machine learning method is used, the threshold processing to be described later is unnecessary, and a candidate pixel of defect can directly be extracted.

In the processing of Step S4, the image processing device 14 executes the second preprocessing on the composite processed image using a frequency filter or the like to generate an image in which the surface defect portion is emphasized. As a result, the processing of Step S4 is completed, and the surface inspection processing proceeds to processing of Step S5.

In the processing of Step S5, the image processing device 14 generates a binarized image by executing the threshold processing on the luminance value of the image obtained by the processing of Step S4. As a result, the processing of Step S5 is completed, and the surface inspection processing proceeds to processing of Step S6.

In the processing of Step S6, the image processing device 14 performs connected/isolated point removal on the binarized image by processing such as expansion/contraction processing as necessary, and then performs labeling processing of labeling adjacent pixels as blobs (specks). Then, the image processing device 14 sets the blobs extracted by the labeling process as surface defect candidate portions. As a result, the processing of Step S6 is completed, and the surface inspection processing proceeds to processing of Step S7.

In the processing of Step S7, the image processing device 14 determines a type and a grade (including harmless) of the surface defect for each of the surface defect candidate portions obtained by the processing of Step S6. As a determination method, a determination rule may be manually decided, or the determination rule may be automatically generated by a general machine learning method using the feature amounts of the regression model (linear regression, logistic regression, multiple regression, support vector machine, nonlinear kernel, and the like), the decision tree model, a random forest, a Bayesian estimation model, the Gaussian mixture model, and a method obtained by boosting these models. In this case, by adding each representative value (an average value, a maximum) of the luminance values of the plurality of spectral images, and a value (a sum, a difference, a ratio) by which each representative value can be compared with each other, and the like to the feature amount, it is possible to perform determination in consideration of the spectral reflection characteristics. In addition, a convolutional neural network may be used as long as a number of pieces of data is sufficient. In addition, a plurality of machine learning methods may be combined. A determination result is displayed on the monitor 15 and used for guidance, or collected in a server and used for determination of availability of shipment and necessity of maintenance of the steel material S. As a result, the processing of Step S7 is completed, and the series of the surface inspection processing ends.

As is clear from the above description, in the surface inspection processing according to the one embodiment of the present invention, the surface of the steel material S is irradiated with light, the reflected light from the surface of the steel material S by the irradiated light is imaged at two or more different wavelength bands, and the surface defect existing on the surface of the steel material S is detected from the information of a relative signal intensity between the plurality of images obtained from the same position on the surface of the steel material S. As a result, the surface defect of the steel material S can be detected completely and accurately. In addition, the presence or absence of the surface defect of the metal material such as the steel material S is investigated using the surface inspection processing according to the one embodiment of the present invention, and quality assurance is performed to confirm whether or not a surface defect occurrence status (an occurrence rate, a size of the defect, and the like) is equal to or less than a predetermined allowable standard. This makes it possible to provide a metal material with a guaranteed surface property. Practically, for example, quality can be guaranteed by describing whether or not the surface defect occurrence status is equal to or less than the predetermined allowable standard in an invoice, an inspection certificate, or the like.

EXAMPLES

First Example

As a first example, an example in which a surface defect of a steel plate was detected using the present invention will be described. The surface defect was in a form of being embedded to a steel plate surface in a manufacturing process of the steel plate, and there existed no uneven portion when viewed from the steel plate surface. In the surface defect of the thick steel plate, a spectral image at the wavelength band of 415 nm and a spectral image at the wavelength band of 750 nm were captured, the luminance correction was performed so that an average value became the same to each other, and the image obtained by taking a difference between the images is illustrated in FIG. 8. The signal of a harmless pattern such as a mill scale is canceled out by taking the difference, and only the signal of the pattern-like defect is emphasized. As a result, it was confirmed that the surface defect could be detected with high accuracy by generating a difference image between a spectral image obtained by capturing light at the longer wavelength and a spectral image obtained by capturing light at the shorter wavelength, utilizing the characteristics of the spectral reflection spectra of a surface defect portion and a sound portion. Depending on manufacturing conditions of the steel plate, a surface layer scale having a surface reflection spectrum similar to that of the surface defect portion may be generated in the sound portion. However, by discriminating the surface defect portion extracted from the difference image using a determiner created by a machine learning method, it is possible to suppress excessive detection and accurately detect the surface defect.

Second Example

Figure 9:
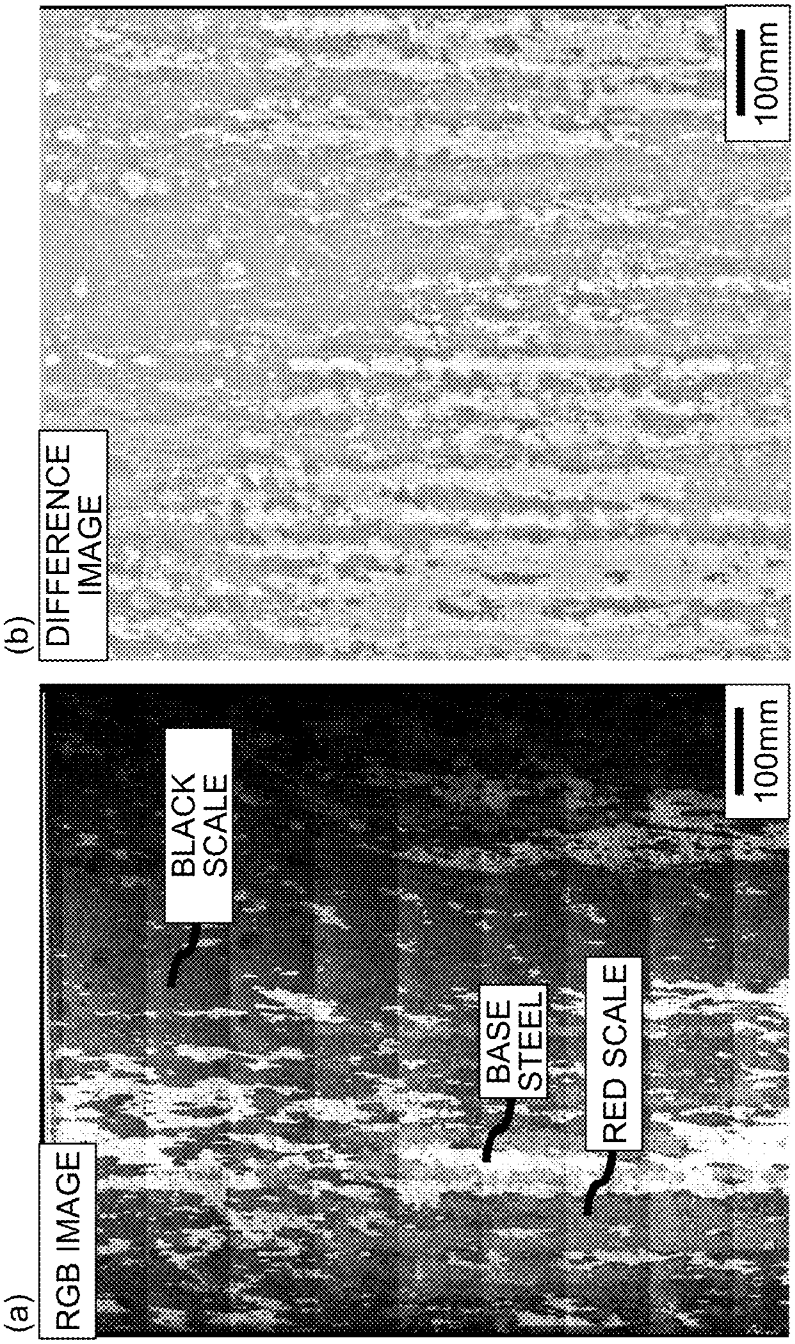
FIG. 9 is a view illustrating one example of a difference image.

As a second example, an example in which a red scale of a steel plate was detected using the present invention will be described. On a surface of the thick steel plate, there exist unevenly a red scale, a black scale, and a base steel portion from which the scale is peeled. The scale of a hot-rolled steel material becomes layered as oxidation progresses, and is often made of wustite (Fed), magnetite ($Fe_3O_4$), and hematite ($Fe_2O_3$) in order of proximity to a base steel. When the scale of the surface is made mainly of wustite or magnetite, a black scale is formed, and the scale is likely to be uniform, to have a high mechanical strength and to be hardly peeled off. When the scale of the surface is made mainly of hematite, a red scale is formed, and the scale is likely to be uniform, to have a low mechanical strength and to be easily peeled. The red scale tends to be avoided because it causes problems in workability, it adheres to equipment in a factory due to its easy peeling property, and it causes stains or unevenness in color tone of a final product, and the red scale may be treated as a kind of surface defect. For a surface image of the steel plate captured by an RGB color camera, luminance correction was performed so that average values of luminance of an R component image and a B component image became the same to each other, and an image obtained by taking a difference between the R component image and the B component image is illustrated in FIGS. 9(*a*), (*b*). A camera and filters were designed so that image capturing could be performed at a narrow wavelength band of 650 nm or more for an R channel and at a narrow wavelength band of 500 nm or less for a B channel. As illustrated in FIGS. 9(*a*), (*b*), it can be seen that signals of the black scale and the base steel portion were canceled out by taking the difference, and only a signal of the red scale was emphasized. From the above, according to the present invention, it was confirmed that the red scale could be accurately detected by creating the difference image between the two-dimensional image obtained by capturing the light at the longer wavelength and the two-dimensional image obtained by capturing the light at the shorter wavelength by utilizing the characteristics of the spectral reflection spectra of the red scale and the black scale. In actual operation, quality assurance can be performed by calculating a ratio and a degree of a red scale generation region with respect to an entire surface of the steel plate, and generation distribution of the red scale can be used for temperature control in a rolling process and abnormality detection of descaling equipment.

Although the embodiments to which the invention made by the present inventors is applied have been described above, the present invention is not limited by the description and drawings constituting a part of the disclosure of the present invention according to the present embodiments. That is, other embodiments, examples, operation techniques, and the like made by those skilled in the art based on the present embodiments are all included in the scope of the present invention.

INDUSTRIAL APPLICABILITY

According to the present invention, a surface inspection method and a surface inspection apparatus for a metal material capable of completely and accurately detecting a surface defect of the metal material can be provided. In addition, according to the present invention, it is possible to provide a high-quality metal material free from surface defects.

REFERENCE SIGNS LIST

1 LINEAR STAGE
2 XENON LIGHT SOURCE
3 SPECTROSCOPIC CAMERA
10, 20 SURFACE INSPECTION APPARATUS FOR METAL MATERIAL
11 LIGHT SOURCE
12 ENCODER, PULSE GENERATOR
13 AREA SENSOR
14 IMAGE PROCESSING DEVICE
15 MONITOR
21 LINE LIGHT SOURCE
22 LINE SENSOR
L ILLUMINATION LIGHT
S STEEL MATERIAL
SA STEEL PLATE SAMPLE

The invention claimed is:

1. A surface inspection method for a metal material in which a surface defect of the metal material is optically detected, the surface inspection method comprising:
- (a) irradiating a surface of the metal material with light;
- (b) obtaining a plurality of images in two or more different wavelength bands by capturing reflected light from a same position on the surface of the metal material by the light emitted in (a); and
- (c) detecting the surface defect present on the surface of the metal material from information of a relative signal intensity between the plurality of images in the two or more different wavelength bands obtained from the same position on the surface of the metal material in (b).

2. The surface inspection method for a metal material according to claim 1, wherein (c) includes detecting the surface defect using a determiner created by a machine learning method using: a relative intensity between the plurality of images as a feature amount; or a plurality of amounts calculated from the relative intensity as the feature amount.

3. The surface inspection method for a metal material according to claim 2, wherein (a) includes irradiating the metal material with the light so that an angle with respect to a normal direction of the surface of the metal material falls within a range of 60° or more and less than 90°, and (b) includes receiving the reflected light so that a light receiving angle with respect to the surface of the metal material falls within a range of 0° or more and less than 20°.

4. The surface inspection method for a metal material according to claim 3, wherein at least one of the two or more different wavelength bands is a wavelength band of 500 nm or less.

5. The surface inspection method for a metal material according to claim 2, wherein at least one of the two or more different wavelength bands is a wavelength band of 500 nm or less.

6. The surface inspection method for a metal material according to claim 2, wherein at least one of the two or more different wavelength bands is a wavelength band of 650 nm or more.

7. The surface inspection method for a metal material according to claim 3, wherein at least one of the two or more different wavelength bands is a wavelength band of 650 nm or more.

8. The surface inspection method for a metal material according to claim 1, wherein (a) includes irradiating the metal material with the light so that an angle with respect to a normal direction of the surface of the metal material falls within a range of 60° or more and less than 90°, and (b) includes receiving the reflected light so that a light receiving angle with respect to the surface of the metal material falls within a range of 0° or more and less than 20°.

9. The surface inspection method for a metal material according to claim 8, wherein at least one of the two or more different wavelength bands is a wavelength band of 500 nm or less.

10. The surface inspection method for a metal material according to claim 8, wherein at least one of the two or more different wavelength bands is a wavelength band of 650 nm or more.

11. The surface inspection method for a metal material according to claim 1, wherein at least one of the two or more different wavelength bands is a wavelength band of 500 nm or less.

12. The surface inspection method for a metal material according to claim 1, wherein at least one of the two or more different wavelength bands is a wavelength band of 650 nm or more.

13. A metal material whose surface property is guaranteed using the surface inspection method for a metal material according to claim 1.

14. The surface inspection method for a metal material according to claim 1, further comprising
- performing a luminance correction on the plurality of images so that average values of luminance in each image become the same; and
- generating a difference image by taking a difference between luminance values of two of the images after performing the luminance correction, wherein
- the surface defect is detected from information of the difference image.

15. The surface inspection method for a metal material according to claim 1, wherein
- the surface of the metal material is irradiated with a single light source that includes components at a plurality of different wavelength bands.

16. A surface inspection apparatus for a metal material that optically detects a surface defect of the metal material, the surface inspection apparatus comprising:

a light source for irradiating a surface of the metal material with light;

an area sensor for obtaining a plurality of images in two or more different wavelength bands by capturing reflected light from a same position on the surface of the metal material by the light emitted by the light source; and an image processing device for detecting the surface defect present on the surface of the metal material from information of a relative signal intensity between the plurality of images in the two or more different wavelength bands obtained from the same position on the surface of the metal material by the area sensor.

17. The surface inspection apparatus for a metal material according to claim 16, wherein the image processing device is further configured to perform a luminance correction on the plurality of images so that average values of luminance in each image become the same, and generate a difference image by taking a difference between luminance values of two of the images after performing the luminance correction, wherein the surface defect is detected from information of the difference image.

18. The surface inspection apparatus for a metal material according to claim 16, wherein the light source is a single light source that includes components at a plurality of different wavelength bands.

* * * * *